(12) United States Patent
Zhu et al.

(10) Patent No.: US 8,019,621 B2
(45) Date of Patent: Sep. 13, 2011

(54) MEDICAL IMAGE REPORT DATA PROCESSING SYSTEM

(75) Inventors: Cynthia Zhu, Livonia, MI (US); Zhong Li, Ann Arbor, MI (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1088 days.

(21) Appl. No.: 11/560,979

(22) Filed: Nov. 17, 2006

(65) Prior Publication Data

US 2007/0237371 A1  Oct. 11, 2007

Related U.S. Application Data

(60) Provisional application No. 60/790,399, filed on Apr. 7, 2006, provisional application No. 60/791,738, filed on Apr. 13, 2006.

(51) Int. Cl.
 *G06Q 10/00* (2006.01)
 *G06Q 50/00* (2006.01)

(52) U.S. Cl. .......................................................... 705/2

(58) Field of Classification Search ................... 705/2, 3
 See application file for complete search history.

(56) References Cited

U.S. PATENT DOCUMENTS

| | | | |
|---|---|---|---|
| 6,725,231 B2 | 4/2004 | Hu et al. | |
| 6,826,578 B2 | 11/2004 | Brackett et al. | |
| 6,950,985 B2 | 9/2005 | Lee | |
| 2002/0016718 A1* | 2/2002 | Rothschild et al. | 705/2 |
| 2002/0143727 A1 | 10/2002 | Hu et al. | |
| 2002/0143824 A1 | 10/2002 | Lee et al. | |
| 2003/0100820 A1 | 5/2003 | Birkhoelzer et al. | |
| 2003/0187689 A1 | 10/2003 | Barnes et al. | |
| 2004/0025110 A1 | 2/2004 | Hu | |
| 2004/0083217 A1 | 4/2004 | Brackett et al. | |
| 2004/0205563 A1 | 10/2004 | Lee | |
| 2005/0004938 A1 | 1/2005 | Koenig | |
| 2005/0021512 A1 | 1/2005 | Koenig | |
| 2005/0108365 A1 | 5/2005 | Becker et al. | |
| 2005/0210063 A1 | 9/2005 | Koenig | |
| 2005/0246629 A1 | 11/2005 | Hu | |

(Continued)

OTHER PUBLICATIONS

W Dean Bidgood Jr., "Clinical Important of the DICOM Structured Reporting Standard", International Journal of Cardiac Imaging, 14: 307-315, 1998.

(Continued)

*Primary Examiner* — Gerald J. O'Connor
*Assistant Examiner* — John Pauls
(74) *Attorney, Agent, or Firm* — Alexander J Burke (57) ABSTRACT

A system uses a flexible mapping capability in adaptively exchanging image related data between a structured report data format and data formats employed by different types of image processing device. A system provides medical image associated measurement data from different types of imaging device in a particular report format data structure. The system includes an acquisition processor for acquiring measurement data associated with medical images produced by an examination of a particular patient using a particular type of imaging device. A repository of mapping information associates clinical terms used by multiple different types of imaging device with corresponding codes compatible with a particular report format data structure employed for providing an imaging examination report of a particular patient. A data processor uses the repository in converting clinical terms in the acquired measurement data provided using the particular type of imaging device to corresponding codes compatible with a particular report format data structure. The data processor processes the codes corresponding to the converted clinical terms as well as elements of the acquired measurement data for incorporation in the particular report format data structure.

18 Claims, 7 Drawing Sheets

U.S. PATENT DOCUMENTS

2006/0064328 A1  3/2006  Datta et al.

OTHER PUBLICATIONS

Cor Loef, "Evidence and diagnostic reporting in the IHE context", International Congress Series 1268 (2004), pp. 108-112.

Thomas Treichel, et al., "Applicability of DICOM structured reporting for the standardized exchange of implantation plans", Int J Cars (2010) 5:1-9.

Rita Noumeir, "Benefits of the DICOM Structured Report", Journal of Digital Imaging, vol. 19, No. 4 (December), 2006: pp. 295-306q.

David A. Clunie, "DICOM Structured Reporting and Cancer Clinical Trials Results", Cancer Informatics 2007: 4 33-56.

W. Dean Bidgood, Jr., "DICOM SR—Requirements—Applications—Benefits", downloaded from http://medical.nema.org/dicom/srag.html; Presented at an SR Workshop organized by NEMA on March 209, 2000.

* cited by examiner

PRIOR ART

MEDICAL IMAGE REPORT DATA PROCESSING SYSTEM

This is a non-provisional application of provisional application Ser. No. 60/790,399 by C. Zhu et al. filed Apr. 7, 2009 and of provisional application Ser. No. 60/791,738 by C. Zhu et al. filed Apr. 13, 2006.

Figure 1:
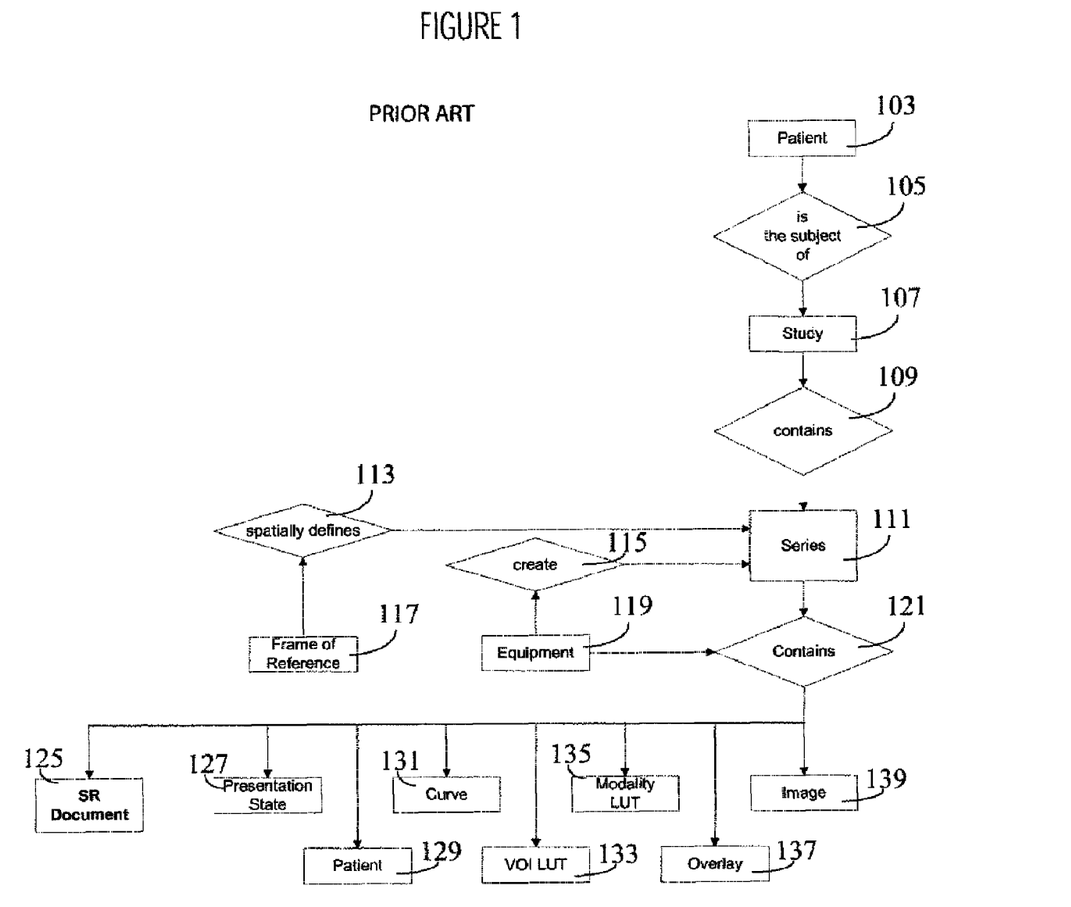
FIG. 1 illustrates a DICOM SR data structure format.
Figure 2:
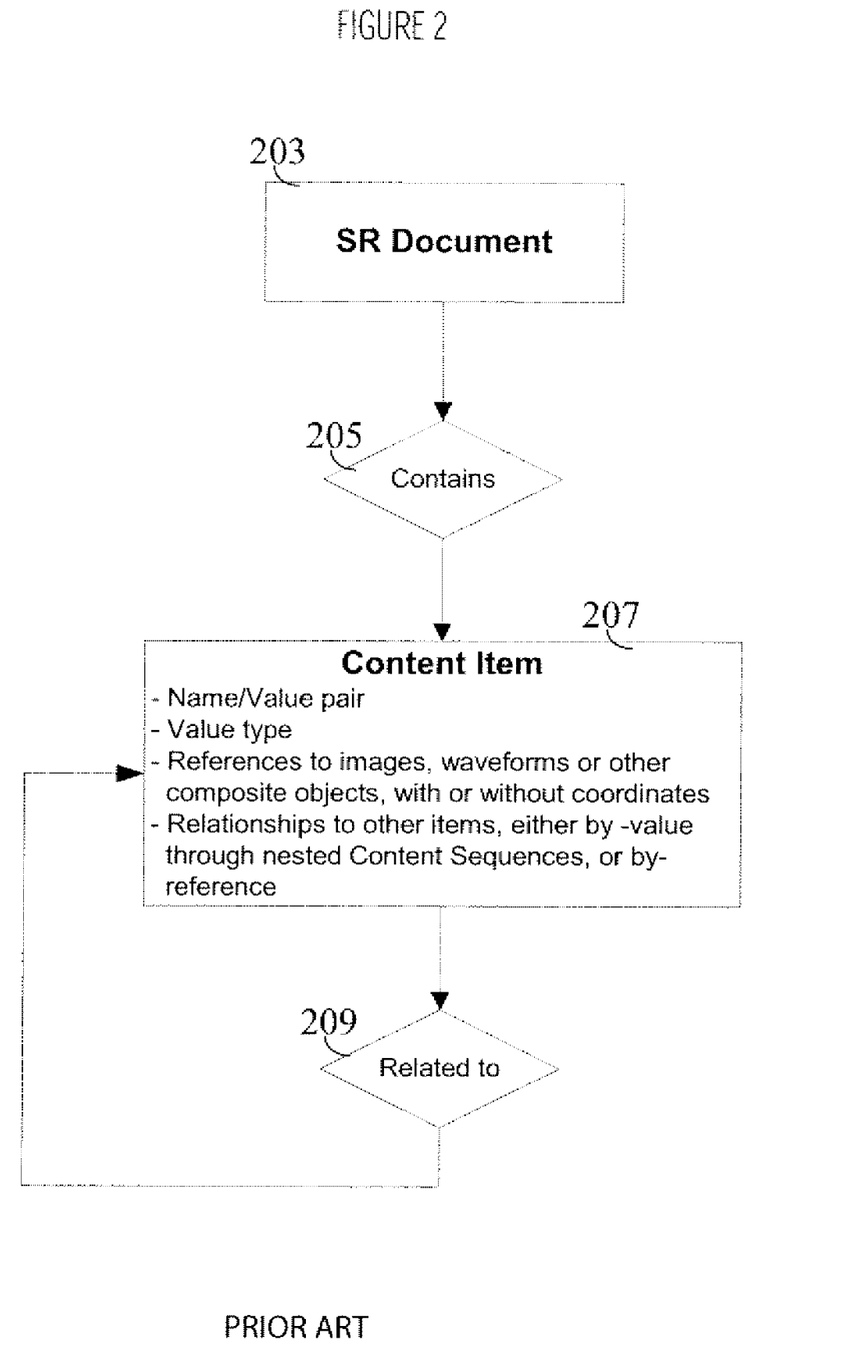
FIG. 2 shows a DICOM SR data structure for conveying medical image associated measurement data from different types of imaging device.

A portion of the disclosure of this patent document contains material which is subject to (copyright or mask work) protection. The (copyright or mask work) owner has no objection to the facsimile reproduction by anyone of the patent disclosure, as it appears in the Patent and Trademark Office patent files or records, but otherwise reserves all (copyright or mask work) rights whatsoever. FIGS. 1 and 2 used herein are protected copyrighted works © Copyright 2004 of the National Electrical Manufacturers Association 1300 N. 17th Street, Rosslyn, Va. 22209 USA and are reprinted with permission of the National Electrical Manufacturers Association.

FIELD OF THE INVENTION

This invention concerns a system for providing medical image associated measurement data, for example, from different types of imaging device in a particular report format data structure.

BACKGROUND OF THE INVENTION

Medical image related and other report data may be generated in a standardized format such as in a Digital and Imaging Communications (DICOM) format suitable for exchange between different systems. A DICOM Structured Report (DICOM SR) format may be used to exchange hierarchical structured content, clinical terminology, and references to images, waveforms or other DICOM composite objects and to exchange image related measurement and calculation data among different systems. However, usage of the DICOM SR format is limited in known medical image data processing and reporting systems. One reason for this is that there is a lack of flexibility in enabling mapping between a DICOM SR data format structure and processing device (platform) specific data format structure. This results in costly (platform) specific development and implementations. Known systems that employ DICOM SR processing typically include DICOM processing support procedures with structured report (SR) support, and SR Content Viewing applications using a generic hierarchical tree view. However, known DICOM SR support procedures offer limited capabilities and fail to provide mapping between different data formats or recognize the advantages of such mappings. DITCOM SR compatible data processing applications typically use proprietary internal mapping functions comprising SR Content Viewing applications that allow a user to specify a desired display format but are not adaptive to processing device data formats and characteristics or requirements. A system according to invention principles addresses these deficiencies and associated problems.

SUMMARY OF THE INVENTION

A system uses a flexible mapping capability in adaptively bidirectionally exchanging image related and other data (such as image measurement data, calculation data and patient record information) between a DICOM SR format and formats employed by different types of image processing device (e.g. ultrasound, CT, MR, X-ray) as well as data formats employed by different versions and manufacturers of a particular type of device. A system provides medical image associated measurement data from different types of imaging device in a particular report format data structure. The system includes an acquisition processor for acquiring measurement data associated with medical images produced by an examination of a particular patient using a particular type of imaging device. A repository of mapping information associates clinical terms used by multiple different types of imaging device with corresponding codes compatible with a particular report format data structure employed for providing an imaging examination report of a particular patient. A data processor uses the repository in converting clinical terms in the acquired measurement data provided using the particular type of imaging device to corresponding codes compatible with a particular report format data structure. The data processor processes the codes corresponding to the converted clinical terms as well as elements of the acquired measurement data for incorporation in the particular report format data structure.

DETAILED DESCRIPTION OF THE INVENTION

Symbols and Abbreviations.
DICOM—Digital Imaging and Communications in Medicine
IOD—Information Object Definitions
DIMSE—DICOM Message Service Element
SOP Class—Service-Object Pair Class. A SOP Class is defined by the union of an IOD and a DIMSE Service Group. An SOP Class definition contains rules and semantics which may restrict the use of the services in a DIMSE Service Group and/or the Attributes of the IOD.
SR—Structured Report.

A soft mapping system according to invention principles provides a bridge supporting exchange of image related data such as image measurement and calculation data) between a structured report data (e.g., a DICOM structured report (SR)) format and data formats employed by different types of image processing device (e.g., ultrasound, CT, MR, X-ray) as well as employed by different versions and manufacturers of a particular type of device. The system supports DICOM compatible encoding and a DICOM SR compatible content tree structure and provides a user friendly SR imaging data reporting interface, which is adaptable to a variety of image processing devices (e.g., different Ultrasound device data structures). DICOM approved Supplement 23 (Structured Reporting Object) in 1999 and multiple Ultrasound Structured Report Templates (Supplement 26, 71, and 72) are part of the DICOM standard, yet there is little usage of DICOM SR data format in exchanging image measurement and calculation data between different imaging devices and applications. The inventors have advantageously recognized that the use of DICOM SR (and other structured data formats) may be promoted by the provision of a flexible data mapping function supporting image related data exchange between a structured reporting format (e.g., a DICOM SR format) and data structures employed by a variety of image processing devices.

An executable application as used herein comprises code or machine readable instruction for implementing predetermined functions including those of an operating system, healthcare information system or other information processing system, for example, in response user command or input. An executable procedure is a segment of code (machine readable instruction), sub-routine, or other distinct section of code or portion of an executable application for performing one or more particular processes and may include performing operations on received input parameters (or in response to received input parameters) and provide resulting output parameters. A processor as used herein is a device and/or set of machine-readable instructions for performing tasks. A processor comprises any one or combination of, hardware, firmware, and/or software. A processor acts upon information by manipulating, analyzing, modifying, converting or transmitting information for use by an executable procedure or an information device, and/or by routing the information to an output device. A processor may use or comprise the capabilities of a controller or microprocessor, for example. A display processor or generator is a known element comprising electronic circuitry or software or a combination of both for generating display images or portions thereof. A user interface comprises one or more display images enabling user interaction with a processor or other device.

As used herein, a report comprises a compilation of data that is produced in response to an imaging examination performed using an MR, CT, X-ray, or Ultrasound device, for example and a report format data structure comprises a data structure. Further, image related and other data includes, image measurement data, calculation data and any information that may be in a patient record.

FIG. 1 illustrates a DICOM SR data structure format used to manage hierarchical structured content, clinical terminology, and references to images, waveforms or other DICOM composite data objects and enhance the precision, clarity and value of clinical documents. In the DICOM structure, a patient (103) is associated (105) with a medical imaging study (107) containing (109) one or more image series (111). An image series (111) is spatially defined (113) using a frame of reference (117) and is created (115) by equipment (119) (e.g., an imaging modality device). An image Study Series may include a DICOM SR compatible document (125) and information indicating a presentation state (127), a patient (129), a curve (131), a value of interest look up table (133), a modality look up table (135), an image overlay (137) and data comprising an individual image (139).

The DICOM standard has defined several SR SOP (Service-Object Pair) classes, including Basic Text SR, Enhanced SR, and Comprehensive SR. They have similar Information Object Definitions (IOD) but have different constraints on contents and relations between content items in a Document Content module. The Document Content Module consists of a single root Content Item that is the root of an SR Document tree. FIG. 2 depicts a DICOM SR data structure for conveying medical image associated measurement data from different types of imaging device, as well as the relationship of SR Documents to Content Items and the relationships of Content Items to other Content Items and to Observation Context. Specifically, the root Content Item 203 has an attribute type of CONTAINER 205, and its Content Sequence (e.g., associated with an image series) conveys other Content Items 207 in the document, either directly or indirectly through further nested Content Sequences. Content items that are related (209) include data item name value pairs, value type indicators, references to images, waveforms or other composite objects, with or without image coordinates. Content items also indicate relationships to other items, either by value, or by reference.

The system advantageously controls the DICOM. SR hierarchical content structure to enable communication between a variety of different image processing devices. The DICOM Standard provides DICOM Templates to constrain a structured report. Users of the DICOM Standard are also able to define specific SR Templates for particular purposes. An SR Template defines a set of constraints on relationships and content (Value Types, Codes, etc.) of Content Items that reference such a Template. A clinical term is defined in a Template with specific Code and Context. Context includes but is not limited to data facilitating traversing a path to an Item from an SR Root Item (e.g., SR document 203) and DICOM Concept Modifiers for the Item.

DICOM SR Documents are generated by various imaging modality devices (e.g., ultrasound, CT, MR, X-ray) or review stations. Imaging modality devices or review stations can also import data from a DICOM SR compatible structured report. However, an imaging modality device or review station may employ an internal data model structure that is different to the DICOM SR data structure. One difference, for example, is that a modality device or review station may use a clinical term that comprises both a unique identifier and also indicates its context. The identifier may be used exclusively by one type of a modality device or by a particular version or manufacturer of a modality device.

Figure 3:
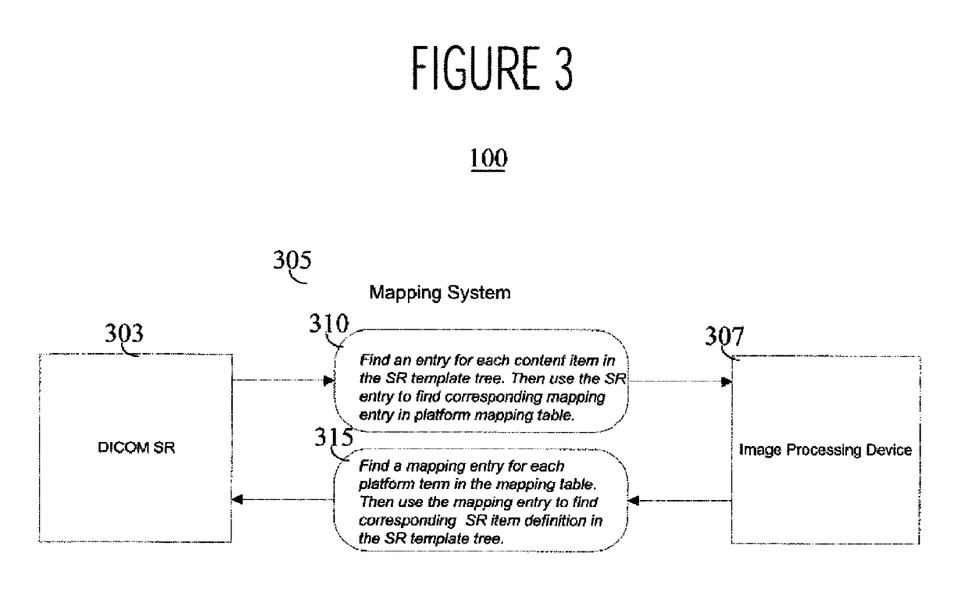
FIG. 3 shows an adaptive system for exchanging medical image associated measurement data between different types of imaging device and a particular report format data structure, according to invention principles.

FIG. 3 shows an adaptive system 100 for exchanging medical image associated measurement data between different types of imaging device and a particular report format data structure. An image processing device or review station uses an interface providing bidirectional data translation in order to read from, or write to, a DICOM SR compatible report. The bidirectional data translation interface employs data mapping and adaptively accommodates different imaging modality devices (e.g., ultrasound, CT, MR, X-ray) or review stations. System 100 employs data mapping tables in the bidirectional data translation interface enabling system 100 to be adaptively scaled to fit the processing device to employ data from a DICOM SR and output data to a DICOM SR. System 100 data mapping is extendible to support different data sets and the mapping is not limited to DICOM SR compatible data items. System 100 adaptively accommodates image processing devices using proprietary data sets and codes for data items, including DICOM SR headings. System 100 also adapts to new versions of applications employed by image processing devices or review stations and supports importing data from a new image processing device model or version without requiring a new system 100 code release. System 100 further adapts to new DICOM SR templates with minimal or no code change. The system 100 adaptability shortens release cycles for image processing devices and review stations.

Bidirectional data translation interface 305 employs data mapping units 310 and 315 in system 100 for adaptively exchanging medical image associated measurement data between different types of imaging device 307 (e.g., ultrasound, CT, MR, X-ray) and a particular report format (e.g., DICOM SR) data structure 303. Mapping units 310 and 315 comprise one or more files in XML (Extensible Markup Language) format. Mapping units 310 and 315 enable data mapping between DICOM SR data structure 303 and an image processing device 307 data structure. Mapping unit 310 identifies an SR Template, containing a section comprising DICOM Concept Modifier definitions, a section of Property definitions, and a template tree structure populated with content item definitions. An individual content item definition specifies Value Type, Relation With Parent, DICOM Concept Code etc. Mapping unit 310 finds an entry for individual content items in a DICOM SR template tree and uses the DICOM SR template entry to find corresponding mapping entries in an image processing device mapping table. An individual entry describes a mapped item and a corresponding item in mapping unit 310, i.e., a DICOM SR template, along with a set of Concept Modifiers. Mapping units 310 and 315 provide bidirectional mapping and data exchange between imaging device 307 and DICOM SR data structure 303.

Bidirectional data translation interface 305 and data mapping units 310 and 315 advantageously enable separation of data mapping and executable application coding. Translation interface 305 is a configuration unit external to executable applications that use it, which facilitates accommodating changes in the executable applications and enables creation of DICOM SR management procedures that are reusable by different image processing devices. Translation interface 305 further advantageously supports new DICOM SR features without requiring new executable application code. In contrast, known systems do not employ an interface like translation interface 305 and instead employ non-adaptive programmed fixed interfaces for a particular image processing which is not flexible and does not readily accommodate future changes. An imaging site may have Ultrasound imaging modality devices produced by various manufacturers and may have different versions of an ultrasound device from a specific manufacturer. The site may employ a central DICOM server and multiple imaging review stations connected to the server. System 100 maps imaging modality device specific data items generated from different Ultrasound modality devices to a host data structure which is processed for an imaging review station to review and manipulate.

Figure 4:
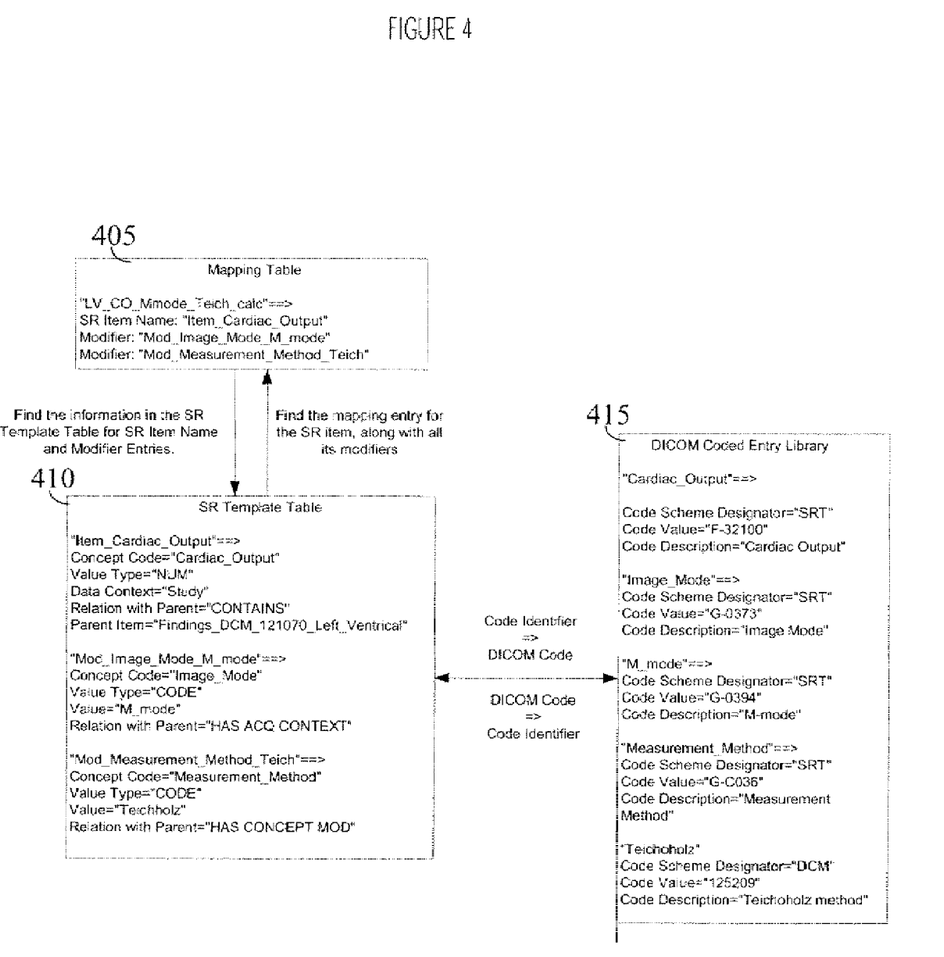
FIG. 4 illustrates data mapping operation enabling exchange of medical image associated measurement and other data between different types of imaging device and a particular report (DICOM SR) format data structure, according to invention principles.

FIG. 4 illustrates data mapping operation in translation interface 305 (FIG. 3) enabling exchange of medical image associated measurement data between different types of imaging device and a particular report (DICOM SR) format data structure, in which an ultrasound station acquires a Cardiac exam and takes multiple measurements. One of the measurements is Cardiac Output. It creates a DICOM SR and adds acquired data to it. DICOM SR Template table 410 implements a DICOM SR hierarchical data tree structure in XML in which individual content item nodes incorporated in the XML hierarchical data structure are assigned corresponding individual identifiers and represent data Content Items. Mapping Table 405 associates an image processing device specific identifier (e.g., a term, LV_CO_Mmode_Teich_calc (Left Ventrical Cardiac Output, M-mode, Teicholz)) with a corresponding DICOM SR representative XML identifier (e.g., a term, Item_Cardiac_Output) and its associated modifiers (e.g. Modifier. Mod_Image_Mode_M_mode).

DICOM SR XML Template table 410 associates identifier terms, e.g., Item_Cardiac_Output with code identifiers (e.g., Cardiac_Output). DICOM SR XML Template table 410 defines Content Items and their relationship in the Template. Individual items are assigned an individual identifier. Template table 410 also has association with code identifiers in DICOM Code Library 415. DICOM Code Library 415 associates code identifiers with corresponding DICOM codes (e.g., Cardiac_Output is associated with Code Scheme Designator SRT, Code Value F-32100, Code Description Cardiac Output). DICOM Code Library 415 maps an element of a DICOM SR compatible item (a code identifier used in Template Table 410) to a corresponding DICOM SR compatible code and corresponding context information identifying characteristics of a particular imaging measurement. The DICOM. Code Library 415 is used in mapping image processing device specific terms to DICOM SR specific terms and vice versa, for example. The mapping system illustrated in units 405, 410 and 415 supports bidirectional exchange of data between a selected image processing device and a DICOM SR data structure. The mapping system enables translation of image processing device specific data to be suitable for incorporation and streaming into a DICOM SR content tree as shown in FIG. 4. DICOM is a standard that specifies how to store clinical data. Sometimes, the clinical data lost their medical meanings in the DICOM format. For example, a doctor doesn't know the place where Cardiac Output is measured until he/she sees the measurement is taken in left ventricle (See Box 410, Item_Cardiac_Output). DICOM SR is a standard to define how the clinical data are logically organized in the DICOM format. In the DICOM SR, the clinical data are structured logically like a tree. DICOM SR describes the meanings of the nodes and leafs in the tree using a DICOM SR template. Since the clinical data and the way to organize the data are different for each clinical practice, DICOM SR developed different templates to address these needs. In the document (See page 11, line 24), we mentioned these templates: Ultrasound OB-Gyn, Ultrasound Vascular and Ultrasound Echo.

Template Table 410 comprises a library of clinical terminologies and DICOM uses a code to refer to an individual clinical term. The system uses unit 410 to identify item "F-32100" (in 415, Cardiac_Output) in a DICOM SR file, as Cardiac Output, for example. The term definition used includes, Code Scheme Designation, Code Value and Code Description. Code Scheme Designation indicates the author determining the meaning of the code; Code Value shows what the value is; Code Description shows what clinical term the code is corresponding to. Individual terms have corresponding individual names, such as, Cardiac_Output, so that it may be readily referenced in other documents, such as, unit 410. In the system, unit 410 describes a DICOM SR template and provides a clinical significant node or leaf in the hierarchical tree data structure a name, such as, Item_Cardiac_Output and Findings_DCM_121070_Left_Ventrical, for easy reference in other documents, such as, Box 405. Box 410 indicates where to find a specific item and also indicates what the item is in a DICOM SR file. For example, Item_Cardiac_Output is found inside Findings_DCM_121070_Left_Ventrical because these items have a child-parent-contains relationship; Item_Cardiac_Output is a numeric value that is used for Cardiac Output in a study; Mod_Image_Mode_M_mode is a code that is used for Image Mode and whose value is M-mode. Unit 405 also defines variables used in a specific medical device by referring to items defined in Unit 410. LV_CO_Mmode_Teich_calc refers to Item_Cardiac_Output, Mod_Image_Mode_M_mode, and Mod_measurement_Method_Teich, for example. Units 410 and 415 indicate that Mod_measurement_Method_Teich is a Cardiac Output using M-image mode and Teicholz measurement method. Units 405, 410 and 415 provide a map to identify and locate information in DICOM SR files for interaction with different types of imaging medical device.

Figure 5:
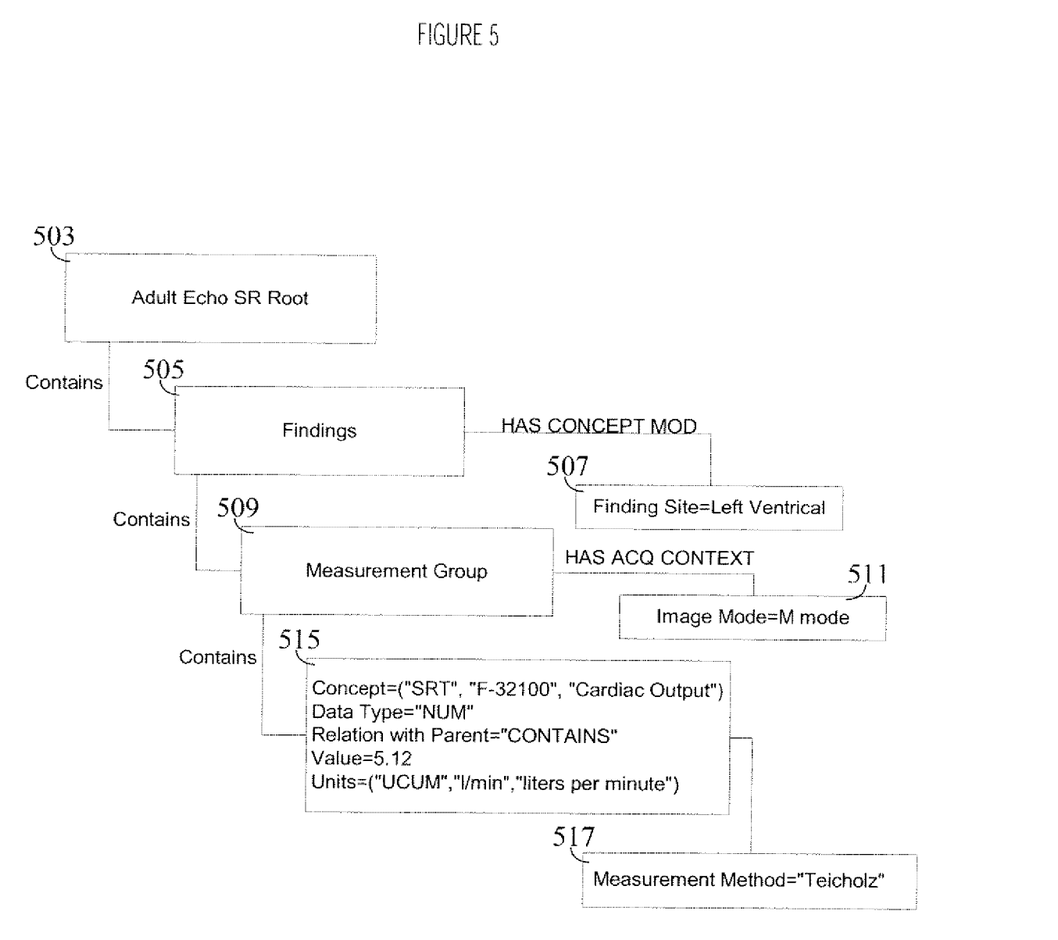
FIG. 5 illustrates a particular (DICOM SR) report format data structure for incorporation of translated medical image associated measurement and other data derived from different types of imaging device, according to invention principles.

FIG. 5 illustrates a particular (DICOM SR) report format data structure for incorporation of translated medical image associated measurement and other data derived from different types of imaging device. Specifically, FIG. 5 illustrates a DICOM SR structure for incorporating an item LV_CO_Mmode_Teich_calc (Left Ventrical Cardiac Output, M-mode, Teicholz). Adult Echo SR root data item 503 contains Findings data item 505 having a modifier 507 indicating a Finding site (left Ventrical). Similarly, Findings data item 505 contains Measurement Group data item 509 having a context item 511 indicating an Ultrasound imaging mode (M mode). Further, Measurement Group data item 509 contains data items 515 comprising Concept (SRT, F-32100, Cardiac Output), Data Type (NUM), Relation with Parent (Contains), Value (5.12) and Units (UCUM, l/min, liters per minute). Data items 515 further are associated a Measurement Method item 517 (Teicholz).

Figure 6:
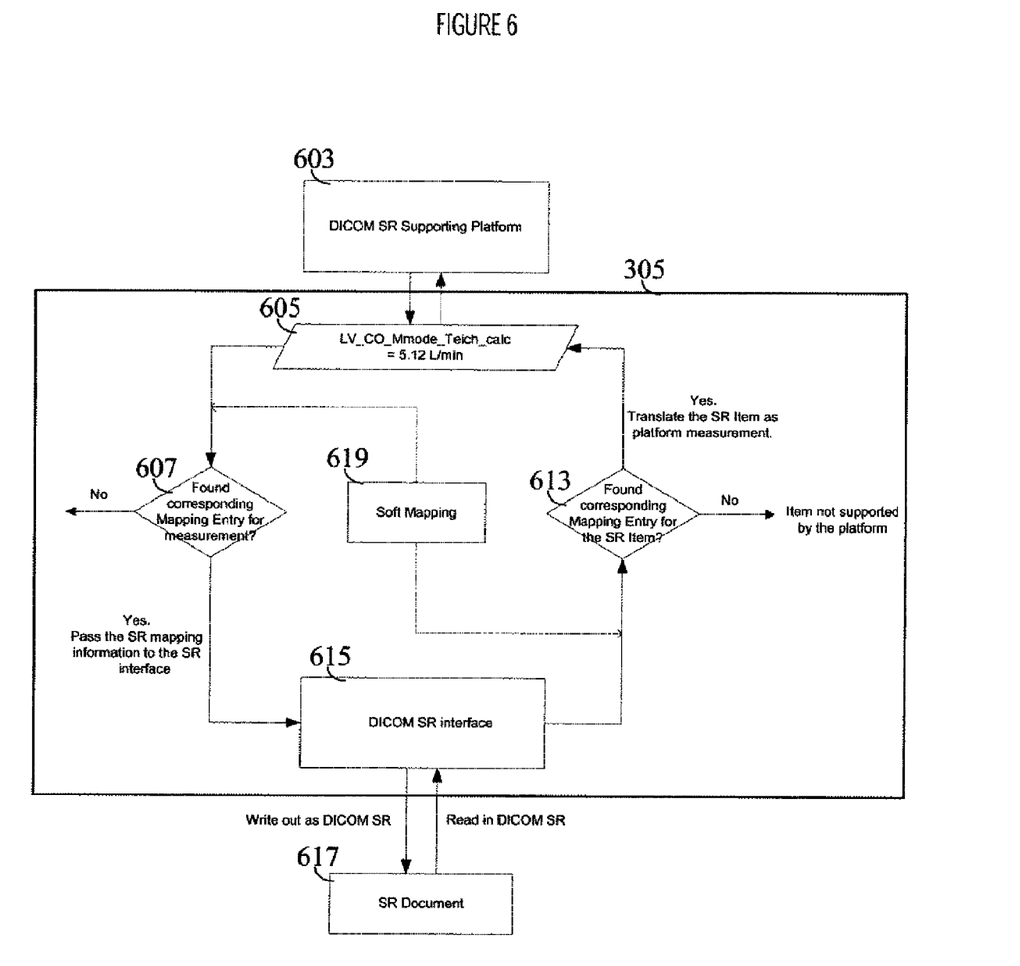
FIG. 6 illustrates data exchange of medical image associated measurement data between an imaging device data format and a particular report format data structure, according to invention principles.

FIG. 6 illustrates data exchange of medical image associated measurement data between an imaging device data format and a particular (DICOM SR) report format data structure and illustrates mapping using interface 305 (FIG. 3) at a device level. Image processing device 603 provides measurement data item 605 (LV_CO_Mmode_Teich_calc (Left Ventrical Cardiac Output, M-mode, Teicholz) having a value 5.12 L per minute) to interface 305. Mapping unit 619 (containing mapping units 405, 410, 415 (FIG. 4)) in interface 305 incorporate definitions for data items supported by image processing device 603 (and other versions and devices) and these data items are structured in a similar manner as the "LV_CO_Mmode_Teich_calc" item in FIG. 5. Mapping unit 619 determines in step 607 whether a corresponding DICOM SR compatible map entry exists for measurement data item 605. If no corresponding entry exists, processing terminates and a next data item from image processing device 603 is processed. In response to unit 619 determining a corresponding DICOM SR compatible map entry exists, DICOM SR interface 615 stores a corresponding DICOM SR compatible mapped data item in SR Document data structure 617 having the hierarchical tree structure shown in FIG. 5.

A DICOM SR data item is read by interface 615 in interface 305 from data structure 617. Mapping unit 619 determines in step 613 that a corresponding map entry (LV_CO_Mmode_Teich_calc) exists for the DICOM SR data item. If no corresponding entry exists, processing terminates and a next data item from DICOM SR data structure 617 is processed. In response to unit 619 determining a corresponding image processing device map entry exists, DICOM SR interface 615 providing corresponding item LV_CO Mmode_Teich calc 607 to image processing device 603.

The mapping system in interface 305 is configurable and adaptable. An image processing device configures mapping data in interface 305 to support exchange of data with a particular data structure. Interface 305 supports multiple different versions and manufacturers of a type of image processing device as well as multiple different types of image processing device (e.g., X-ray, MR, CT, Ultrasound). The data structure (e.g., DICOM SR) interface mapping data is shared by multiple different image processing devices and is extensible and configurable by an image processing device to meet device specific requirements (since the DICOM Standard may not fulfill requirements). The interface 305 napping system is configurable to enable an image processing device to support new DICOM SR features without requiring a new code release. For example, in response to a release of a new set of DICOM Concept Codes for various data Items, Mapping unit 405, 410, 415 (FIG. 4) XML files in unit 619 are modified to produce an up to date DICOM SR data structure. Interface 305 also supports importing data items by an image processing device from DICOM SR compatible objects created by different systems. In response to an image processing device (a source platform) generating a DICOM SR compatible report incorporating changed clinical data item codes, for example, interface 305 provides data mapping enabling an image review station (a destination reading platform) to accommodate the changed clinical data item codes without software re-programming. The interface 305 data Mapping XML files are adapted enabling the changed clinical data item codes to be processed and incorporated in a data structure suitable for access and processing by the image review station.

A DICOM SR data structure may contain data other than image measurements such as clinical terminologies and references to DICOM composite objects, including calculations, assessments, patient history references to images, waveforms or other DICOM composite objects, for example. The interface 305 mapping system may be used for both writing out, and reading in, DICOM SR compatible (and other structure) data when used in imaging modality devices (MR, CT etc.), for example. When the interface 305 mapping system is used in a post-processing system (e.g., a single or multi-modality image review station), the mapping system is used for reading DICOM SR compatible data generated from another imaging modality device. Types of imaging examination supported by DICOM SR may not be associated with a modality and may include, Ultrasound OB-Gyn, Ultrasound Vascular, Ultrasound Echo, Catheterization procedure, Mammography, Chest CAD, and Breast imaging, for example. Further, image measurements may or may not have one or more context data items and parent node context, i.e., a location or path in a DICOM SR compatible data structure.

Interface 305 provides flexible data mapping using XML to advantageously define mappings and a DICOM SR content tree with a relatively fine precision, for example, and is able to define a complete DICOM M SR Template structure and also supports proprietary DICOM SR templates. Interface 305 makes fixing structural problems quick and relatively easy. Further, interface 305 supports various DICOM SR templates without the necessity of new software programming and allows users to specify a DICOM SR content tree structure and maps data from multiple different image processing devices requiring device model specific mapping and device version specific mapping. In contrast, known system mapping files provide minimal structure.

Figure 7:
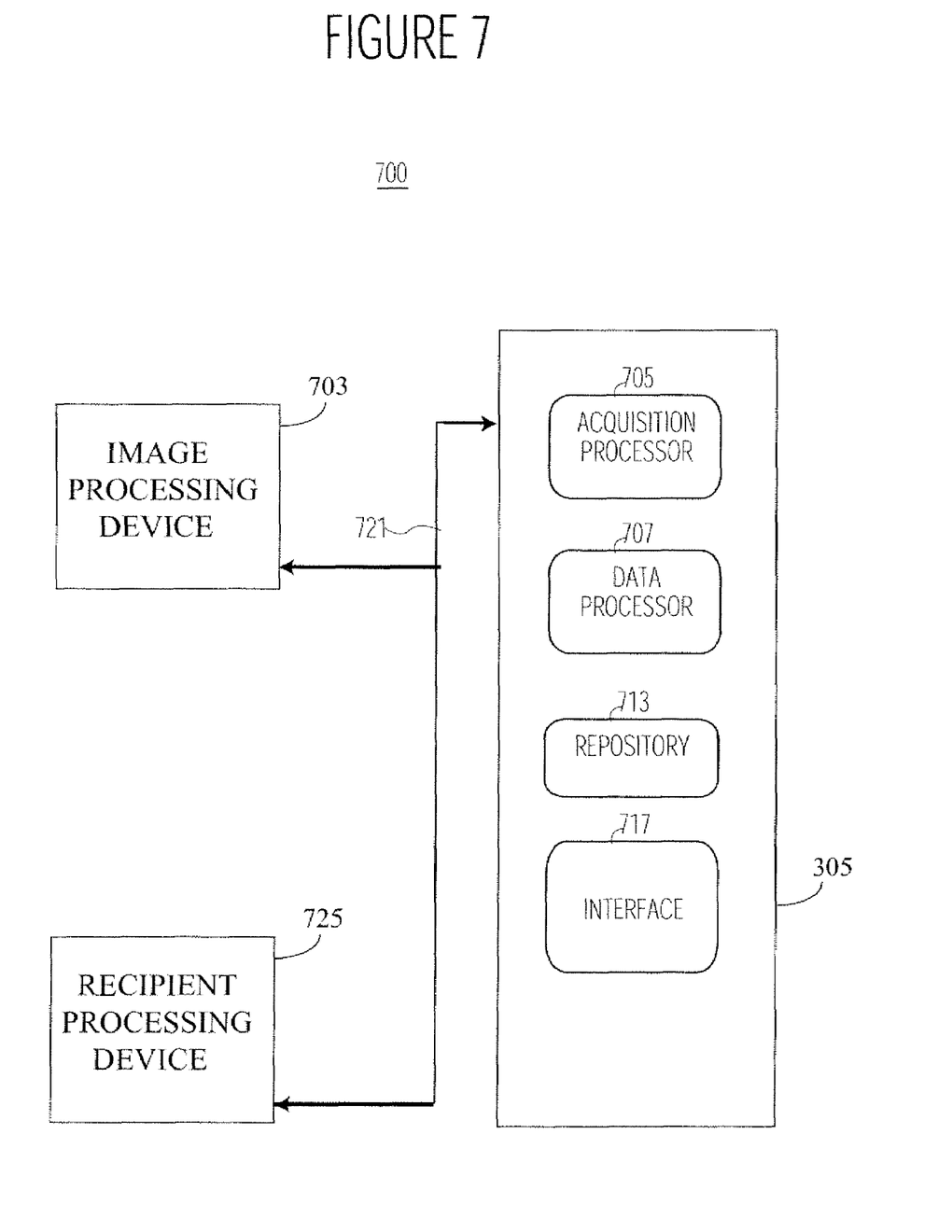
FIG. 7 shows an adaptive system for providing medical image associated ancillary data from different types of imaging device in a particular report format data structure, according to invention principles.

FIG. 7 shows adaptive system 700 including interface 305 for providing medical image associated ancillary data from different types of imaging device in a particular report format data structure (e.g., a DICOM SR compatible data structure). The medical image associated ancillary data includes image related measurements, calculations, clinical terminologies, references to DICOM composite objects, assessments, patient history, references to images, waveforms or other DICOM composite objects. Acquisition processor 705 in interface 305 acquires ancillary data (e.g., measurement data) associated with medical images produced by an examination of a particular patient using a particular type of imaging device 703 via network 721. Mapping information repository 713 associates clinical terms used by multiple different types of imaging device and/or multiple different types of imaging examination, with corresponding codes compatible with a particular report format data structure employed for providing an imaging examination report of a particular patient. The mapping information is used for both writing out a DICOM SR compatible report and reading data from a DICOM SR compatible report. In one embodiment, the mapping information includes, first mapping information mapping associating clinical terms used by a plurality of different types of imaging device to corresponding DICOM SR compatible items and second mapping information mapping an element of a DICOM SR compatible item to a corresponding DICOM SR compatible code and corresponding context information identifying characteristics of a particular imaging measurement.

The multiple different types of imaging device comprise at least two of, an MRI device, a CT scan device, an X-ray device, an Ultrasound device and a nuclear imaging device. In another embodiment the multiple different types of imaging device comprise at least one of, (a) a single type of imaging modality device provided by different manufacturers comprising, an MRI device, a CT scan device, an X-ray device, an Ultrasound device or a nuclear imaging device and (b) different versions of a single type of imaging modality device provided by a single manufacturer.

Data processor 707 uses mapping information repository 713 in converting clinical terms in the acquired ancillary (e.g., measurement) data provided using the particular type of imaging device 703 (or particular type of imaging examination) to corresponding codes compatible with a particular report format data structure. The corresponding codes include context information associated with characteristics of a particular imaging measurement and compatible with the particular report format. Further, the mapping information in repository 713 associates clinical terms used by multiple different types of imaging device (or multiple different types of imaging examination) with corresponding codes and corresponding context information. The characteristics of a particular imaging measurement include data value, units if applicable, and its context. Data context may include one or more of (but are not limited to) the following, a type of imaging view, a type of imaging mode, a type of imaging method and parent nodes context indicating location or path in a DICOM SR compatible data structure. The characteristics may also include, Measurement Method, Type of Derivation, Finding Site, Laterality, Topographical modifiers. Normality, Level of Significance, Selection Status, Statistical Properties (Measurement range, Population description, Reference Authority). Further, the multiple different types of imaging examination include two or more of, (a) Ultrasound OB-Gyn, (b) Ultrasound Vascular, (c) Ultrasound Echo, (d) a Catheterization procedure, (e) Mammography, (f) Chest CAD, and (g) Breast Imaging. Data processor 707 also uses repository 713 in processing the codes corresponding to the converted clinical terms as well as elements of the acquired ancillary data for incorporation in the particular report format data structure. Interface 717 communicates the particular report format data structure to recipient device 725 in response to user command.

The systems and image menus of FIGS. 1-7 are not exclusive. Other systems, and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. Functions, processes or activities connected with FIGS. 3 and 7 may be performed automatically or alternatively, wholly or partially in response to manual interaction. A system according to invention principles monitors and processes document deficiencies and automatically manages tasks and creates and provides forms online for addressing and removing document deficiencies. Further, any of the functions and steps provided in the systems of FIGS. 3 and 7 may be implemented in hardware, software or a combination of both and may reside on one or more processing devices located at any location of a network linking depicted elements or another linked network including another intra-net or the Internet.

What is claimed is:

1. A system for providing medical image associated measurement data from different types of imaging device in a particular report format data structure, comprising:
   at least one processing device including,
      an acquisition processor configured to acquire measurement data associated with medical images produced by an examination of a particular patient using a particular type of imaging device;
      a repository of a plurality of device type and imaging examination type specific mapping information includes imaging device type specific clinical terms of a plurality of different types of imaging devices and a plurality of different types of imaging examinations used in a plurality of corresponding different device type specific first report format structures, said mapping information associating imaging device type specific clinical terms of a plurality of different types of imaging devices and a plurality of different types of imaging examinations with corresponding codes compatible with a different second report format data structure employed for providing an imaging examination report of a particular patient, an imaging device type specific clinical term of said plurality of different types of imaging device comprising data identifying in at least one of, (a) a measurement method, (b) a measured parameter type identifier and (c) and an imaging mode of a specific imaging modality type; and
      a data processor for configured to,
         use said mapping information in converting clinical terms in said acquired measurement data in a first report format structure provided using said particular type of imaging device and a particular type of imaging examination to corresponding codes compatible with said different second report format data structure and for
         process said codes corresponding to said converted clinical terms as well as elements of said acquired measurement data for incorporation in said second report format data structure.

2. A system according to claim 1, wherein
   an imaging device type specific clinical term of said plurality of different types of imaging device comprises data identifying at least two of, (a) a measurement method, (b) a measured parameter type identifier and (c) and an imaging mode of a specific imaging modality type and
   said different second report format data structure comprises a DICOM SR compatible data structure and
   said first report format structure is incompatible with a DICOM SR compatible format data structure.

3. A system according to claim 1, wherein
said mapping information associates said plurality of different types of imaging examination with corresponding codes and
said plurality of different types of imaging device comprise at least one of, (a) a single type of imaging modality device provided by different manufacturers and (b) different versions of a single type of imaging modality device provided by a single manufacturer.

4. A system according to claim 3, wherein
said single type of imaging modality device comprises one of, (a) an MRI device, (b) a CT scan device, (c) an X-ray device, (d) an Ultrasound device and (e) a nuclear imaging device.

5. A system according to claim 1, wherein
said plurality of different types of imaging device comprise at least two of, (a) an MRI device, (b) a CT scan device, (c) an X-ray device, (d) an Ultrasound device and (e) a nuclear imaging device.

6. A system according to claim 1, including
an interface for communicating said second report format data structure to a recipient device in response to user command.

7. A system according to claim 1, wherein
said corresponding codes include context information compatible with said second report format, said context information being associated with characteristics of a particular imaging measurement and
said mapping information associates clinical terms used by a plurality of different types of imaging device with corresponding codes and corresponding context information.

8. A system according to claim 7, wherein
said characteristics of a particular imaging measurement include data indicating at least one of, (a) a type of imaging view, (b) a type of imaging mode and (c) a type of imaging method, (d) a Measurement Method, (e) a Type of Derivation, (f) a Finding Site, (g) Laterality, (h) Topographical modifiers and (i) Normality.

9. A system according to claim 7, wherein
said characteristics of a particular imaging measurement include DICOM compatible data indicating at least one of, (a) a type of imaging view, (b) a type of imaging mode and (c) a type of imaging method.

10. A system according to claim 1, wherein
said mapping information includes,
    first mapping information mapping associating clinical terms used by a plurality of different types of imaging device to corresponding DICOM SR compatible items and
    second mapping information mapping an element of a DICOM SR compatible item to a corresponding DICOM SR compatible code and corresponding context information identifying characteristics of a particular imaging measurement.

11. A system for providing medical image associated ancillary data from different types of imaging device in a particular report format data structure, comprising:
at least one processing device including,
    an acquisition processor configured to acquire ancillary data associated with medical images produced by a particular type of imaging examination of a particular patient;
    a repository of a plurality of device type and imaging examination type specific mapping information includes imaging device type specific clinical terms of a plurality of different types of imaging devices and a plurality of different types of imaging examination used in a plurality of corresponding different device type specific first report format structures, said mapping information associating imaging device type specific clinical terms of a plurality of different types of imaging examination with corresponding codes compatible with a DICOM SR compatible second report format data structure employed for providing an imaging examination report of a particular patient and different from a first report format structure incompatible with a DICOM SR format structure, an imaging device type specific clinical term of said plurality of different types of imaging device comprising data identifying at least one of, (a) a measurement method, (b) a measured parameter type identifier and (c) and an imaging mode of a specific imaging modality type; and
    a data processor configured to,
        use said mapping information in converting clinical terms in said acquired ancillary data in said first report format structure and provided using said particular type of imaging examination to corresponding codes compatible with said DICOM SR different second report format data structure and for
        process said codes corresponding to said converted clinical terms as well as elements of said acquired ancillary data for incorporation in said second report format data structure.

12. A system according to claim 11, wherein
an imaging device type specific clinical term of said plurality of different types of imaging device comprises data identifying a measurement method and a measured parameter type identifier and
said ancillary data includes data associated with at least one of, (a) calculations, (b) assessments, (c) patient history, (d) references to images, (d) waveforms and (e) other DICOM composite objects.

13. A system according to claim 11, wherein
said ancillary data comprises clinical terminologies and references to DICOM composite objects.

14. A system according to claim 11, wherein
said mapping information is used for both writing out a DICOM SR compatible report and reading data from a DICOM SR compatible report.

15. A system according to claim 11, wherein
said plurality of different types of imaging examination include two or more of, (a) Ultrasound OB-Gyn, (b) Ultrasound Vascular, (c) Ultrasound Echo, (d) a Catheterization procedure, (e) Mammography, (f) Chest CAD, and (g) Breast Imaging.

16. A system according to claim 11, wherein
said corresponding codes include context information compatible with said DICOM SR compatible second report format, said context information being associated with characteristics of a particular imaging measurement,
said mapping information associates clinical terms used in a plurality of different types of imaging examination with corresponding codes and corresponding context information and
said characteristics of a particular imaging measurement include data indicating at least one of (a) a type of imaging view, (b) a type of imaging mode, (c) a type of imaging method and (d) parent nodes context indicating location or path in a DICOM SR compatible data structure.

17. A method for providing medical image associated measurement data from different types of imaging device in a particular report format data structure, comprising the activities of:
employing at least one processing device for,
acquiring measurement data associated with medical images produced by an examination of a particular patient using a particular type of imaging device;
storing, in a repository, a plurality of device type and imaging examination type specific mapping information including imaging device type specific clinical terms of a plurality of different types of imaging device and a plurality of different types of imaging examinations used in a plurality of corresponding different device type specific first report format structures, said mapping information associating imaging device type specific clinical terms of a plurality of different types of imaging device and a plurality of different types of imaging examinations with corresponding codes compatible with a different second report format data structure employed for providing an imaging examination report of a particular patient, an imaging device type specific clinical term of said plurality of different types of imaging device comprising data identifying at least one of, (a) a measurement method, (b) a measured parameter type identifier and (c) and an imaging mode of a specific imaging modality type;
using said mapping information in converting clinical terms in said acquired measurement data in a first report format structure provided using said particular type of imaging device and a particular type of imaging examination to corresponding codes compatible with said different second report format data structure; and
processing said codes corresponding to said converted clinical terms as well as elements of said acquired measurement data for incorporation in said second report format data structure.

18. A method according to claim 17, wherein
an imaging device type specific clinical term of said plurality of different types of imaging device comprises data identifying a measurement method and a measured parameter type identifier.

* * * * *